United States Patent [19]

Gelfer et al.

[11] 4,338,923

[45] Jul. 13, 1982

[54] INFLATABLE-CELL TYPE BODY TREATING APPARATUS

[75] Inventors: Vadim Gelfer; Yaakov Kaganovsky, both of Ramat Gan; Shimon Muchnik, Tel Aviv; Shimshon Shmuter, Ramat Gan, all of Israel

[73] Assignee: Mego Afek Industrial Measuring Instruments, Afek, Israel

[21] Appl. No.: 217,041

[22] Filed: Dec. 16, 1980

Related U.S. Application Data

[63] Continuation of Ser. No. 945,796, Sep. 26, 1978, abandoned.

[30] Foreign Application Priority Data

Oct. 13, 1977 [IL] Israel ........................................ 53123

[51] Int. Cl.$^3$ ................................................ A61M 1/00

[52] U.S. Cl. ......................... 128/24 R; 128/DIG. 20; 128/DIG. 25

[58] Field of Search ............... 128/DIG. 20, DIG. 25, 128/24 R; 137/625.11, 625.18, 624.2

[56] References Cited

U.S. PATENT DOCUMENTS

| | | | |
|---|---|---|---|
| 1,608,239 | 11/1926 | Rosett | 128/24 R |
| 2,533,504 | 12/1950 | Poor | 120/24 R |
| 2,741,265 | 4/1956 | Poor | 137/625.11 |
| 2,781,041 | 2/1957 | Weinberg | 128/60 |
| 3,469,602 | 9/1969 | Wiley | 137/624.2 |
| 4,013,069 | 3/1977 | Hasty | 128/DIG. 15 |
| 4,156,425 | 5/1979 | Arkans | 128/24 R |

FOREIGN PATENT DOCUMENTS

| | | | |
|---|---|---|---|
| 964553 | 3/1975 | Canada | 137/625.11 |
| 1175948 | 4/1959 | France | 128/24 R |
| 2246260 | 6/1975 | France | 128/24 R |

*Primary Examiner*—Stephen C. Pellegrino
*Assistant Examiner*—J. L. Kruter
*Attorney, Agent, or Firm*—Benjamin J. Barish

[57] ABSTRACT

Apparatus is described for the treatment of edema, comprising a substantially flat inflatable band divided into a plurality of internal inflatable cells extending along one dimension of the band, and wrappable about the body part to be treated to form a sleeve with the inflatable cells extending annularly around the sleeve, the inflatable cells being in partially overlapping relationship widthwise of the band. The band is made of three strips of resilient sheet material bonded to each other along spaced bond lines to define the partially overlapping inflatable cells.

8 Claims, 13 Drawing Figures

INFLATABLE-CELL TYPE BODY TREATING APPARATUS

RELATED APPLICATION

The present application is a continuation of our Patent Application Ser. No. 945,796, filed Sept. 26, 1978, now abandoned.

BACKGROUND OF THE INVENTION

The present invention relates to apparatus for the treatment of body parts, and particularly to apparatus for the treatment of edema, namely the excessive accummulation of fluid in body tissues.

It has been found that beneficial results can be obtained in treating edema by sequentially compressing successive portions of the afflicted body part, usually an upper or lower limb, to produce a messaging or pumping action towards the heart. One type of apparatus designed for this purpose is described in U.S. Patent 2,781,041, which apparatus includes a sleeve for enclosing the body part, the sleeve being made up of separate inflatable cells in end-to-end relationship, an inner inflatable cell within and embracing the separate cells, and means for successively inflating the cells. Another type of apparatus is described in French Pat. Nos. 1,175,948 and 2,246,260, in which the sleeve is provided with inflatable cells in partially overlapping relationship. Further constructions are illustrated in U.S. Pat. Nos. 4,013,069 and 4,156,425.

SUMMARY OF THE INVENTION

An object of the present invention is to provide apparatus of the foregoing type but having advantages over the known prior art, as will be discussed more particularly below.

According to one aspect of the present invention, there is provided apparatus for the treatment of body parts, comprising an inflatable sleeve of flexible material divided into a plurality of internal inflatable cells extending along one dimension of the sleeve, each of said cells including a port for inletting and outletting fluid with respect thereto, thereby to individually inflate or deflate the cells; said sleeve being applicable to the body part to be treated to enclose same with the inflatable cells extending annularly around the sleeve; inflating means for applying a pressurized fluid to said ports according to a predetermined sequence for inflating and deflating said internal cells; said inflating means comprising a source of pressurized fluid, a rotary distributor including a pressurized chamber connected to the pressurized fluid source, a drain chamber vented to the atmosphere, and passageways coupling the pressurized and drain chambers to the ports of the inflatable cells according to a predetermined sequence during the rotation of the distributor; and an interchangeable apertured selector plate between the rotary distributor and the inflatable cell ports to select the ports to receive the pressurized fluid.

The latter features provide a high degree of flexibility with respect to the sequencer and speed of inflation and deflation of the band cells, and the band sizes with which the apparatus can be used.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF THE PREFERRED EMBODIMENT

Figure 1:
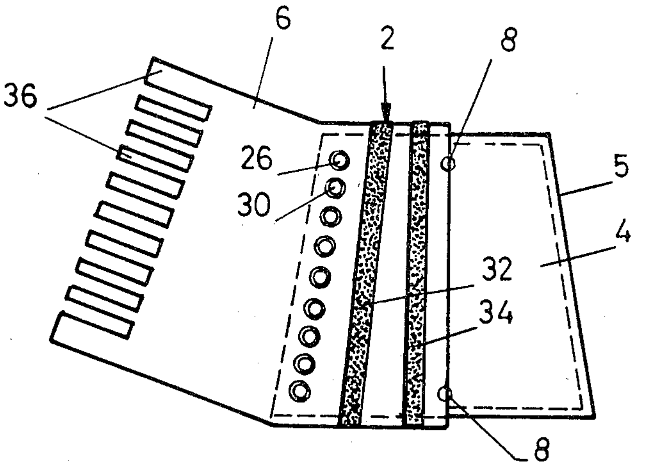
FIG. 1 illustrates one form of band assembly constructed in accordance with the invention for application to the body part being treated, FIG. 1*a* being a fragmentary view illustrating the opposite face of the fingers used in the band assembly of FIG. 1.

The construction of the inflatable band portion of the described apparatus is particularly illustrated in FIGS. 1–5: The complete band assembly, generally designated 2 in FIG. 1, comprises an inflatable band 4, a cloth cover strip 5, and a retaining band 6 for wrapping the inflatable band about the body part to be treated. The inflatable band 4 is originally in a flat condition and is constituted of strips of resilient sheet material, such as of rubber, bonded to each other in a manner to be described more particularly below with respect to FIGS. 4 and 5, to form a plurality of separate inflatable cells which are in partially overlapping relationship to each other. The cover strip 5 is of cloth and forms an outer removable cover for the inflatable band 4. The retaining band 6 is also of cloth and is secured at one end to a mid-portion of the inflatable band 4, as by clips 8. In use, the inflatable band 4 is wrapped around the body part to be treated, and the retainer band 6 is then wrapped around the inflatable band 6 and is secured at its ends to cover the inflatable band and to retain it in its wrapped condition.

Figure 4:
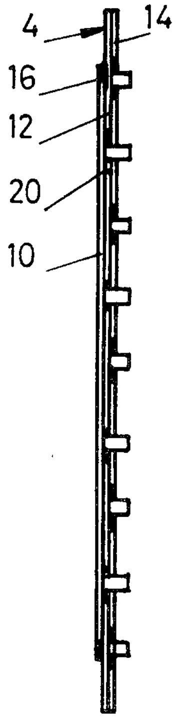
FIG. 4 is an enlarged longitudinal sectional view along lines IV—IV of FIG. 3, showing the cells in their depressurized or deflated condition.
Figure 5:
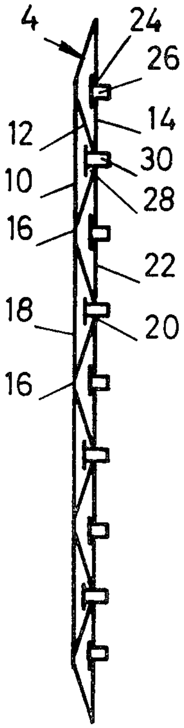
FIG. 5 is a view corresponding to that of FIG. 4 but showing the cells in their pressurized or inflated condition.
Figure 3:
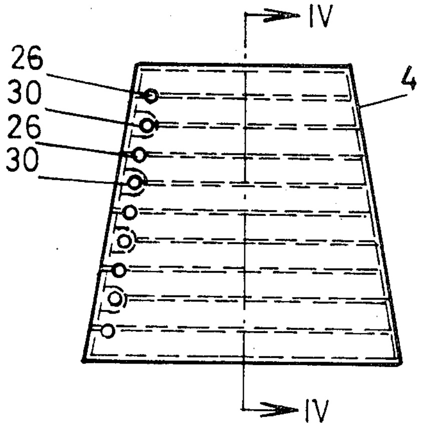
FIG. 3 illustrates the inflatable band of FIG. 2 without its outer cloth cover strip.

As shown in FIGS. 4 and 5, three strips of resilient sheet material are used in making the inflatable band 4, namely an inner strip 10, an intermediate strip 12, and an outer strip 14. The inner strip 10 is bonded to the intermediate strip 12 along a plurality of spaced bond lines 16 to define a first group of internal cells or compartments 18 between the two strips and extending lengthwise thereof. The outer strip 14 is similarly bonded to the intermediate strip 12 along a plurality of spaced parallel bond lines 20 to form a second group of internal cells or compartments 22 lengthwise of the strips. However, the latter bond lines 20 are in staggered relationship with respect to bond lines 16, whereby the second group of internal cells 22 are in partially overlapping relationship with respect to the first group of cells 18 widthwise of the strips. Further, the outer strip 14 is formed with a plurality of ports 24 each including a connector 26 for applying pressurizing fluid (e.g. air) to inflate and deflate the cell 22; and the intermediate strip 12 includes a similar plurality of ports 28 having connectors 30 for inflating and deflating the cells 18. As particularly shown in FIGS. 1–3, the connectors 26 and 30 are arranged in a line, with the connectors 26 of the outer strip ports 24 alternating with the connectors 30 of the intermediate strip ports 28. The inflatable band 4 is covered by a removable cloth cover 5 provided with openings to receive the connectors 26 and 30.

FIG. 4 illustrates the above construction of the inflatable band 4 in its non-inflated condition; and FIG. 5 illustrates the condition of the band 4 when its cells are inflated by a pressurized fluid introduced through the connectors 26, 30 of ports 24, 28.

Figure 1A:
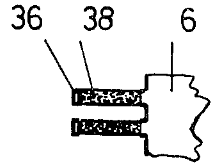
Figure 2:
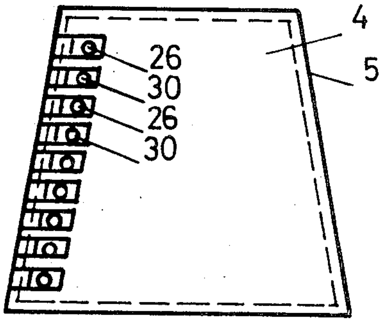
FIG. 2 illustrates the inflatable band portion of the assembly of FIG. 1 including its outer cloth cover strip.

The retainer band 6 is also of cloth and carries a pair of interlocking fibrous strips 32, 34 (e.g. of "Velcro", Reg.T.M), adjacent to the end to which it is secured to the cover 5 of the inflatable band 4 by means of the clips 8. The interlocking fibrous strips 32, 34, extend in spaced parallel relationship to each other in the same direction as the linear array of the port connectors 26, 30. The opposite end of the retainer band 6 is formed with a plurality of fingers 36 whose lower faces (as shown in FIG. 1*a*) carry further interlocking fibrous strips 38 adapted to engage and to be interlocked with strips 32 and 34.

Thus, in order to apply the inflatable band assembly 2 to a body part, such as a leg to be treated, the inflatable band 4 (including its cloth cover 5) is placed against and wrapped around the leg, and then the outer retaining band 6 is wrapped around to enclose the inflatable band 4. Band 6 is retained in its wrapped condition by causing the fibrous interlocking strips 38 of fingers 36 to interlock with strips 32, 34 carried at the opposite end of the retainer band 6.

It will be seen that the foregoing construction of the band assembly 2 provides a number of important advantages over the prior known constructions. Thus, since the band is constructed in a flat condition so as to be wrappable around the limb to be treated, rather than being a sleeve slipped over the limb, it can be used to accommodate limbs of different sizes. In addition, it can also be used in a non-sleeve configuration, to treat body parts other than limbs, for example backs or shoulders, by pressing the inflatable band section 4 against the body part to be treated. In addition, the novel construction provides inflatable cells in an overlapping relationship thereby producing a more effective wave-like pumping action with respect to the body part being treated.

Figure 6:
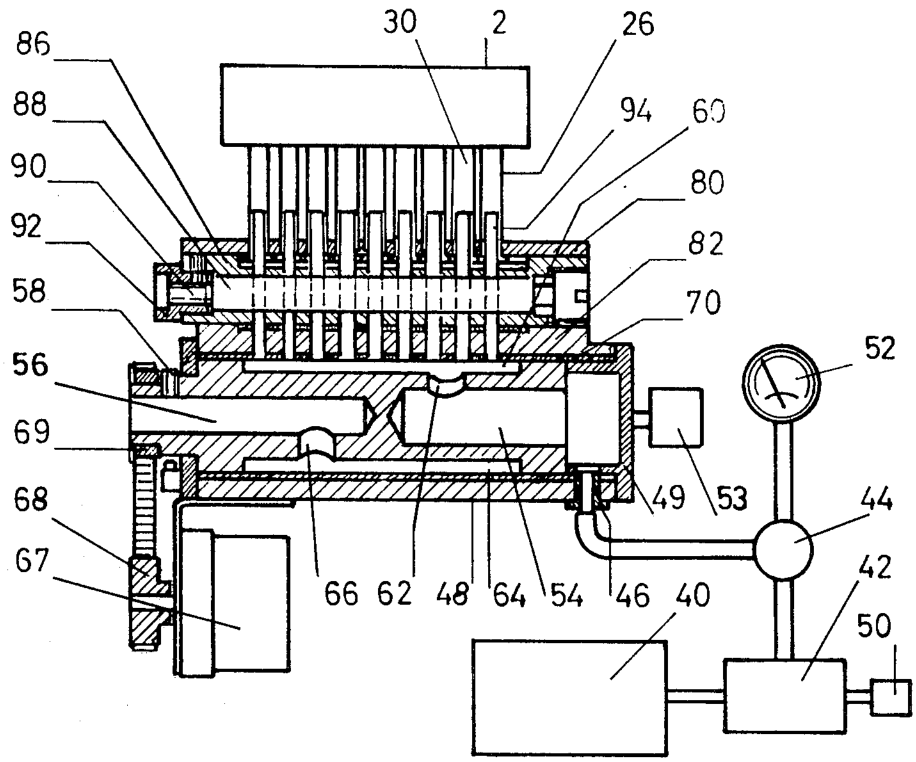
FIG. 6 is a longitudinal sectional view particularly illustrating the means for supplying pressurized fluid to the inflatable band cells in sequence.
Figure 7:
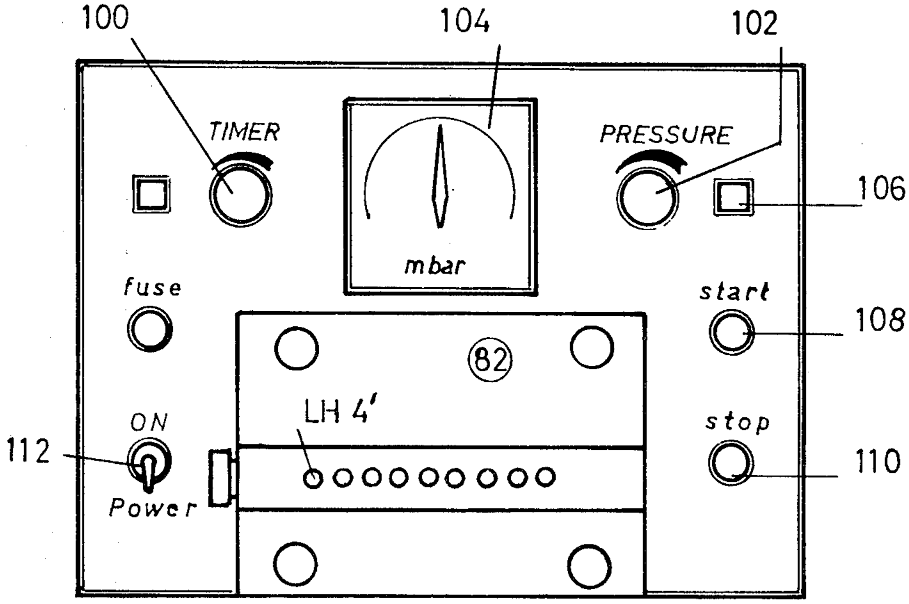
FIG. 7 is a top plan view of the pressurized fluid supply of FIG. 6, particularly illustrating the outlet fluid connections to the inflatable band and the various controls and indicators on the face panel of the apparatus.

The complete apparatus, including the inflatable band assembly 2 and particularly the inflating unit for inflating the band cells, is illustrated in FIG. 6. FIG. 7 is a top plan view illustrating the inflating unit of the apparatus including the various indicators and controls, whereas the remaining figures illustrate different portions of the inflating unit and two possible sequences of inflation-deflation which may be used.

With reference to FIG. 6, the apparatus comprises an air compressor 40 connected to a receiver 42 which directs the compressed air via a reduction valve 44 to the inlet port 46 of a rotary distributor, generally designated 48, rotatably mounted within a fixed housing 49. A safety valve 50 is connected to the receiver 42, a manometer 52 is connected to the reduction valve 44, and a relief valve 53 is connected to the distributor 48.

The rotary distributor 48 is formed with a pressurized chamber 54 communicating with the inlet port 46, and with a depressurized chamber 56 connected by a vent 58 to the atmosphere. The outer surface of the rotary distributor 48 is formed with a first recess 60 communicating by a passageway 62 with the pressurized chamber 54, and with a further recess 64 communicating by a passageway 66 with the depressurized chamber 56.

Rotary distributor 48 is rotated during the operation of the apparatus by means of an electric motor 67 driving a wheel 68 coupled by a belt to another wheel 69 fixed to the end of the rotary distributor. It will be seen that as the rotary distributor 48 is rotated, its recess 60 is always under high pressure via its connection 62 to the pressurized chamber 54, and its recess surface 64 is always under atmospheric pressure via its connection 66 to the depressurized or vented chamber 56.

Figure 8:
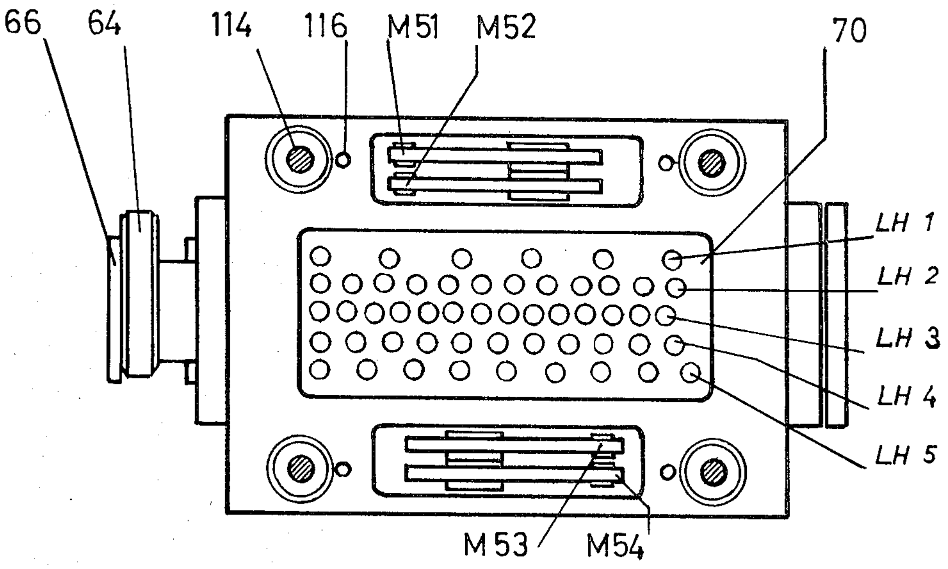
FIG. 8 is a plan view of the compressor and distributor portion of the apparatus illustrated in FIG. 7.

A cover plate 70 (See FIG. 8) is attached to the fixed housing 49 of the rotary distributor 48 to overlie recesses 60 and 64 as the distributor is rotated. Fixed cover plate 70 is formed with a plurality of lines of holes LH1, LH2–LH5, each line including a different number of holes. Thus, line LH1 includes five holes, line LH2 includes eleven holes,-and LH5 includes seven holes. Cover plate 70 is ranged so that all the holes will be successively aligned with the high pressure recess 60 and the low pressure recess 64 during the rotation of the distributor 48.

Figure 9:
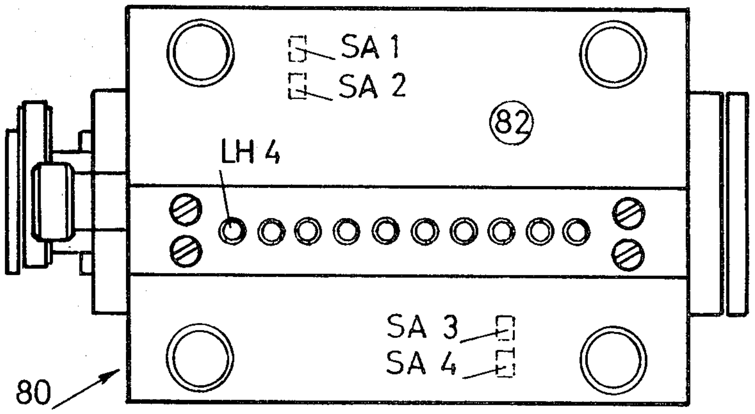
FIG. 9 is a plan view of the regulator portion of the apparatus of FIG. 7.

A selector and regulator unit 80, particularly illustrated in FIG. 9, is adapted to be attached to the rotary distributor unit 48. Unit 80 includes a selector plate 82 having but a single line of holes corresponding in number and spacing to one of the lines of holes LH1–LH5 in cover plate 70 so as to select the line of holes to be used for any particular operation. For purposes of example, selector plate 82 is illustrated in FIG. 9 as having a line of holes LH4' consisting of 9 holes corresponding to the line of holes LH4 in cover plate 70.

In addition to the selector plate 82, unit 80 also includes a regulator assembly which is effective to regulate the flow of the compressed fluid from the rotary distributor to the inflatable band 2. This regulator comprises a regulator sleeve 86 and a stem 88, both being formed with apertures corresponding in number and spacing to the holes in the selector plate 82. The apertures formed in the regulator stem 88 and the regulator sleeve 86 may be aligned with each other to provide for maximum flow of pressurized fluid therethrough and to the inflatable band 2. Stem 88, however, may be displaced in the axial direction with respect to sleeve 86 so as to produce a predetermined misalignment between their apertures, and thereby to regulate the flow of the fluid to the ports of the inflatable band 2. The axial displacement of the regulator stem 88 may be effected by a pin 90 threaded into an end wall 92 of unit 80, the end of pin 90 moving stem 88 axially of the regulator with the rotation of the pin.

The outer end of the apertured regulator sleeve 86 receives connectors 94 aligned with its apertures and adapted to be connected to the connectors 26, 30 of the inflatable band 2.

FIG. 7 illustrates the fluid supply unit including the selector plate 82 for selecting the line of holes LH4′ as described above with respect to FIG. 9. In addition, FIG. 7 illustrates the various controls and indicators on the face panel of this unit, these including: a timer 100 which can control the inflation rhythm or repetition rate by changing the speed of motor 60, a pressure-regulator control 102 which fixes the inlet pressure by controlling reduction valve 44, a pressure indicator 104, a "Power on" indicator 106, a "Start" push-button 108, a "Stop" push-button 110, and a "Power on" switch 112.

For simplifying the presetting operation, it is desirable to enable the selector plate 82 itself to determine the speed of operation of the motor distributor 60, since the use of the unit with an inflatable band having a larger number of cells (e.g. corresponding to the line of holes LH3 in FIG. 8) would normally require the distributor motor 60 to be operated at a higher speed. For this purpose, the distributor motor 60 may be controlled by four microswitches MS1–MS4 which are selectively actuatable by switch actuators SA1–SA4 in the form of square pins, one or all of which are carried on the rear face of the different selector plates 82 (FIG. 9) in position to selectively actuate the microswitches when the selector plate is attached to the cover plate of the pressurizing unit. The attachment is made by a plurality of assembly pins 114 (FIG. 8), registration being effected by locating pins 116.

Figure 10:
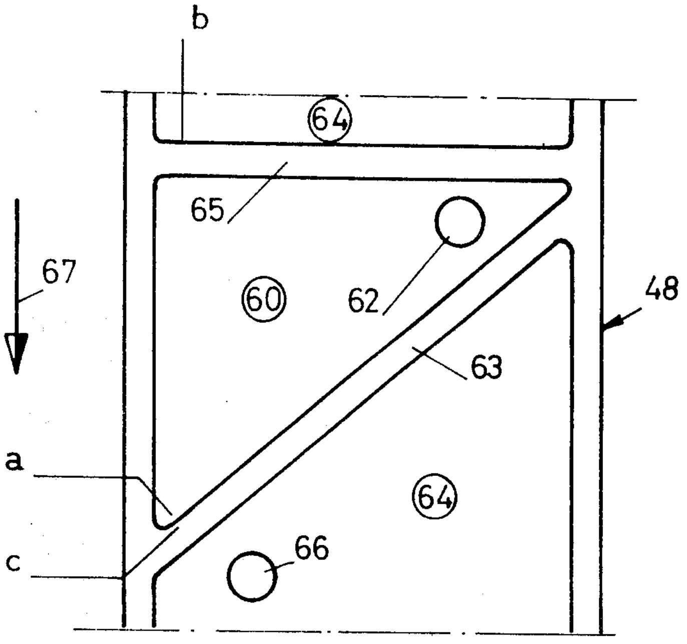
FIGS. 10 and 11 illustrate two possible constructions of rotary distributors to produce two different sequences of inflation and deflation; and depressurizing the band compartments, as illustrated in FIG. 10.
Figure 11:
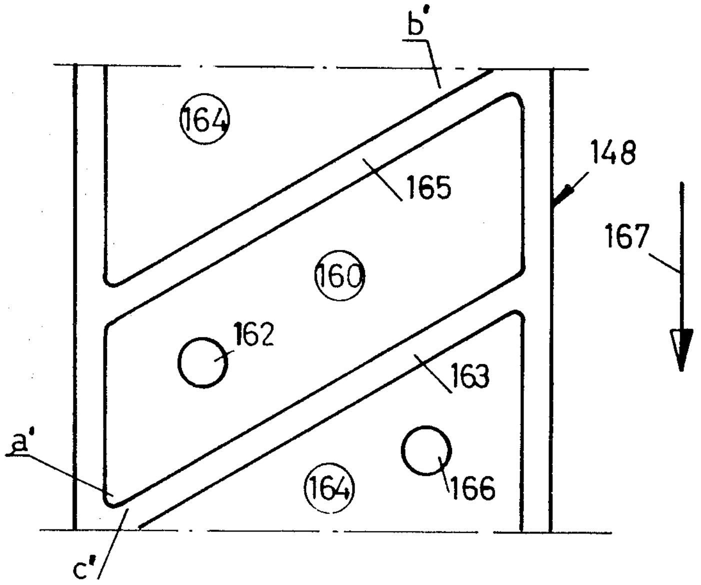
Figure 12:
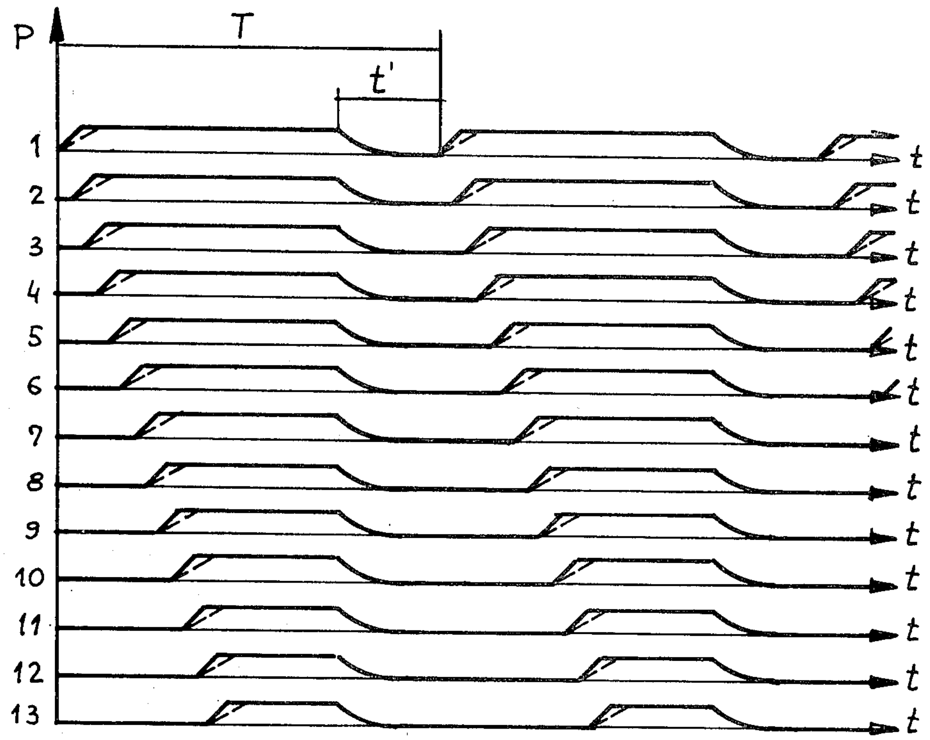
FIGS. 12 and 13 illustrate the sequence of inflation and deflation produced by the rotary distributor constructions of FIGS. 10 and 11, respectively.
Figure 13:
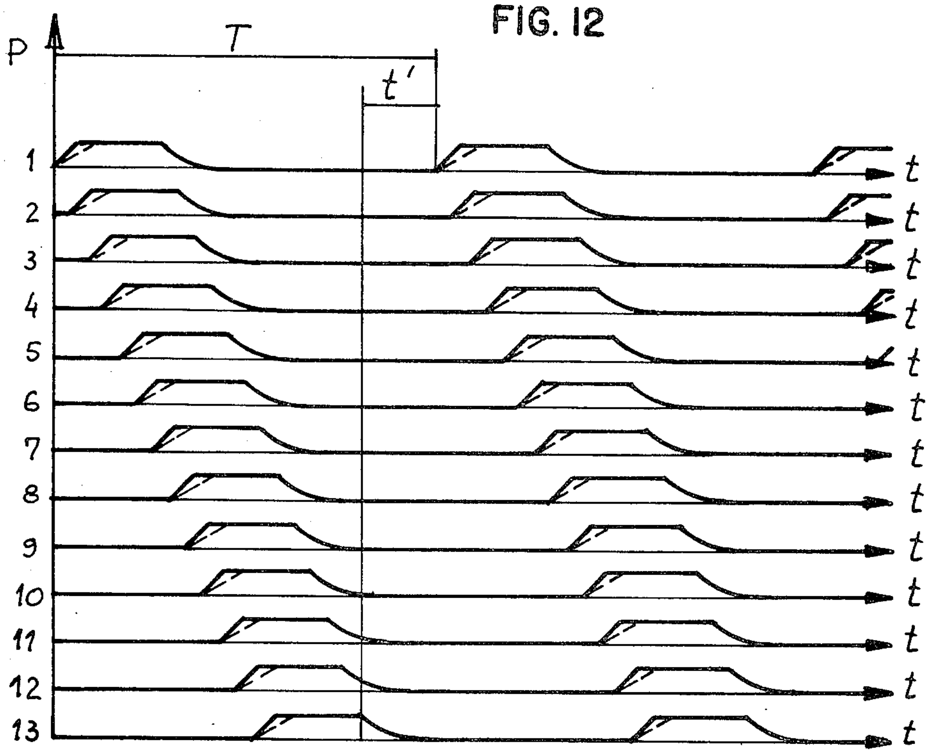

The operation of the apparatus will now be described particularly with reference to FIGS. 10 and 11 illustrating two possible constructions of the rotary distributor 48, and the timing diagrams of FIGS. 12 and 13 illustrating the inflation-deflation sequences produced by the two constructions of FIGS. 10 and 11 respectively.

As indicated above, when the compressor 40 is operated and the rotary distributor 48 is rotated by its drive motor 60, recess 60 will be continuously subjected to the high pressure of chamber 54 of the rotary distributor, and recess 64 will be continuously subjected to the low or atmospheric pressure of chamber 56. Thus, the holes LH1–LH5 (FIG. 8) of the fixed cover plate 70 on the rotary distributor unit 48 will be successively subjected to the high and low pressure of these recesses. The line of holes LH1–LH5 selected to be operative during any particular operation of the apparatus is determined by the selector plate 82 used in the selector and regulator unit 80. For purposes of example, the description below, and the timing diagrams of FIGS. 12 and 13, assume that a 13-hole line (namely LH3) is selected by the selector plate 82. Accordingly, only the 13-holes of line LH3 will be operative, during the rotation of distributor 48, to pass the pressurized fluid to the cells (13 in this example) of the inflatable band 2 in order to inflate them, and to drain the fluid from the cells in order to deflate them.

The sequence of inflating and deflating the cells is determined by the arrangement of recesses 60 and 64 in the rotary distributor 48. FIG. 10 illustrates one arrangement of recesses which will produce the inflation-deflation sequence illustrated in FIG. 12. Thus, the rotary distributor 48 will rotate with respect to the 13 aligned holes LH4 in cover plate 70 and selector plate 82 such that surface 63 of the distributor will intercept the line of holes during the movement of the distributor from its low-pressure recess 64 to its high-pressure recess 60, and surface 65 of the distributor will intercept the line of holes when the distributor moves from its high-pressure recess 60 to its low-pressure recess 64. As shown in FIG. 10, surface 63 is inclined with respect to the direction of rotation of the distributor (indicated by arrow 67), so that the initiation of the inflation of the band cells will be sequential, one right after the other. On the other hand, since surface 65 is at right angles to the direction of rotation of the distributor, the initiation of the deflation of the band cells will occur substantially at the same point in the cycle. Thus, the inflation-deflation timing or rhythm using the rotary distributor construction of FIG. 10, will be that illustrated in FIG. 12, wherein point a in FIGS. 10 and 12 marks the beginning of the sequential inflation of the cells, point b marks the end of the inflations and the beginning of the deflations, and point c marks the beginning of the sequential reinflations of the cells. It will thus be seen that a pause or dwell interval (t, FIG. 12) occurs in each cycle (T) in which all the cells are in a deflated condition, this dwell occurring from points c-a. It has been found that providing such a pause or dwell interval in which all the band cells are in a deflated condition enhances blood circulation and the messaging effect produced by the apparatus.

On the other hand, if the rotary distributor arrangement illustrated in FIG. 11 is used, it will be seen that the inflation-deflation timing illustrated in FIG. 13 will be produced. Thus, the initiation of the inflation of the cells will also be sequential since surface 163 of the rotary distributor 148 separating its low pressure recess 164 from its high pressure recess 160 is inclined with respect to the direction of rotation (arrow 167) of the distributor as in FIG. 10. However, surface 165 of the distributor in the arrangement of FIG. 11 is also inclined with respect to the direction of rotation of the distributor, so that the initiation of the deflation of the cells will not be simultaneous, as in FIG. 12, but will also be sequential. This is shown in the diagram of FIG. 13, wherein it will be seen that point a′ marks the beginning of the sequential inflations, point b′ marks the end of the inflations and the beginning of the sequential deflations, and point c′ marks the beginning of the next sequential inflations. A similar pause or dwell interval is provided, indicated as t′ in FIG. 13, when all the cells are in their deflated condition, this pause occurring from point c′–a′ in FIG. 11.

The speed of inflation and deflation of the band cells may be predetermined by the regulator unit 84, namely by presetting the degree of misalignment between the apertures in the regulator stem 86 and regulator sleeve 88, this being done by threading pir 90 to axially displace the stem the desired amount. This misalignment determines the crosssectional area of the passageways from the pressurized fluid source to the band cells, and thereby the rate of inflation and deflation of the band cells. The latter controls the shape of the leading edges in the inflation and deflation rhythm, which is shown by broken lines in the diagrams of FIGS. 12 and 13.

It will thus be seen that a very versatile apparatus is provided permitting the operator: to select the number of band cells to be inflated and deflated (by the appropriate selection of selector plate 82) according to the number of band cells to be operative in any particular application; to preset the speed of inflation and deflation (by threaded pin 90); to select the desired inflation-deflation sequence of the band cells (by the recess configuration of the distributor 48); and to preset the rhythm of inflation-deflation by the timer 100.

What is claimed is:

1. Apparatus for the treatment of body parts, comprising an inflatable sleeve of flexible material divided into a plurality of internal inflatable cells extending along one dimension of the sleeve, each of said cells including a port for inletting and outletting fluid with respect thereto, thereby to individually inflate or deflate the cells; said sleeve being applicable to the body part to be treated to enclose same with the inflatable cells extending annularly around the sleeve; inflating means for applying a pressurized fluid to said ports according to a predetermined sequence for inflating and deflating said internal cells; said inflating means comprising a source of pressurized fluid, a rotary distributor including a pressurized chamber connected to the pressurized fluid source, a drain chamber vented to the atmosphere, and passageways coupling the pressurized and drain chambers to the ports of the inflatable cells according to a predetermined sequence during the rotation of the distributor; and an interchangeable apertured selector plate between the rotary distributor and the inflatable cell ports to select the ports to receive the pressurized fluid.

2. Apparatus according to claim 1, wherein said sleeve comprises a wrappable band including three strips of resilient sheet material bonded to each other in overlying relationship; the inner strip being bonded to the intermediate strip along a first plurality of spaced bond lines to define a first group of said inflatable cells therebetween; the outer strip being bonded to the intermediate strip along a second plurality of spaced bond lines which are staggered with respect to the first plurality of bond lines to define a second group of said inflatable cells in staggered, partially overlapping relationship with respect to the first group of cells.

3. Apparatus according to claim 2, wherein said ports are arranged in a line with alternating ones being formed in said outer strip and the remaining alternating ones being formed in said intermediate strip.

4. Apparatus according to claim 2, wherein said retaining means comprises a retaining band attached to one end to said inflatable band and including securing means at its opposite end for securing same when wrapped with the band around the body part to be treated.

5. Apparatus according to claim 4, wherein said securing means comprises an interlocking fibrous strip carried by said opposite end of said retaining band and engageable with an other interlocking fibrous strip carried by said one end of said retaining band.

6. Apparatus according to claim 5, wherein said securing means includes a plurality of spaced fingers formed at said opposite end of the retaining band parallel to the wrapping direction, each finger carrying an interlocking fibrous strip on one face, said other interlocking fibrous strip being substantially at a right angle to said fingers.

7. Apparatus according to claim 1, wherein said inflating means further comprises a regulator interposed between said distributor and said ports to regulate the flow of fluid thereto, and thereby to regulate the speed of inflation and deflation of the inflatable cells.

8. Apparatus according to claim 7, wherein said regulator comprises a regulator sleeve disposed between the distributor and the inflatable band ports and formed with a plurality of apertures establishing communication therebetween, a stem within the sleeve and formed with a like plurality of apertures alignable with the apertures of the regulator sleeve, and means for displacing the stem axially of the sleeve to produce a predetermined misalignment between their apertures to regulate the flow of the fluid from the distributor sleeve to the inflatable band ports.

* * * * *